United States Patent
Wilson et al.

(10) Patent No.: US 6,737,395 B1
(45) Date of Patent: May 18, 2004

(54) METHOD OF REDUCING OR PREVENTING MALODOUR

(75) Inventors: Craig S. Wilson, Kent (GB); Tony Minhas, Kent (GB); John M. Behan, Kent (GB)

(73) Assignee: Quest International B.V., Naarden (NL)

( * ) Notice: Subject to any disclaimer, the term of this patent is extended or adjusted under 35 U.S.C. 154(b) by 0 days.

(21) Appl. No.: 09/743,089

(22) PCT Filed: Jul. 6, 1999

(86) PCT No.: PCT/GB99/02165

§ 371 (c)(1),
(2), (4) Date: Jan. 5, 2001

(87) PCT Pub. No.: WO00/01356

PCT Pub. Date: Jan. 13, 2000

(30) Foreign Application Priority Data

Jul. 7, 1998 (GB) ............................................. 9814653

(51) Int. Cl.⁷ ................................................. A61K 7/46
(52) U.S. Cl. ........................................... 512/1; 424/76.4
(58) Field of Search .............................. 512/1; 424/76.4

(56) References Cited

U.S. PATENT DOCUMENTS 3,969,259 A  *  7/1976  Lages .......................... 510/101
5,420,104 A     5/1995  Holzner et al.
5,554,588 A     9/1996  Behan et al.

FOREIGN PATENT DOCUMENTS

EP  126 944    12/1984
GB  1 575 380   9/1980

OTHER PUBLICATIONS

Lacoste, et al: "Les Proprietes Antiseptiques De L'Huile Essentielle De Lippia Sidoides Cham. Application a La Microflore Cutanee", Ann. Pharmaceutiques Francaises, vol. 54, No. 5, 1996 pp. 228–230 XP002120135, the whole document.

Morris et al: "Antimicrobial Activity of Aroma Chemicals and Essential Oils", Journal of the American Oil Chemists' Society, May 1, 1979, p. 595, para 1–para 3, table III.

Fiedler: Antimikrobielle Wirkung Von Aromastoffen Und Aetherische Ole Seifen–Ole–Fette–Wachse, vol. 107, No. 3, 1981, pp. 15–76, XP002120136, p. 75–p. 76.

* cited by examiner

Primary Examiner—Jill Warden
Assistant Examiner—Monique T. Cole
(74) Attorney, Agent, or Firm—Morgan, Lewis & Bockius LLP

(57) ABSTRACT

A method for reducing or preventing body malodour by topically applying to human skin perfumery materials capable of inhibiting the production of malodorous metabolites caused by micro-organisms comprising corynebacteria. The perfumery materials are capable of inactivating corynebacteria capable of catabolising fatty acids.

4 Claims, No Drawings

METHOD OF REDUCING OR PREVENTING MALODOUR

This application is the national phase of International application PCT/GB99/02165 filed Jul. 6, 1999, which designated the U.S. and that international application was published under PCT Article 21(2) in English.

This invention relates to perfume components, mixtures thereof and perfume compositions, to personal products and detergent products containing such perfumes, and to a method and the use of such perfumes and products to deliver a deodorant effect.

In particular, it relates to perfume components, mixtures thereof, and perfume compositions for inhibiting the production of odorous metabolites by topically applying to human skin perfumery components capable of inhibiting the production of body malodour caused by micro-organisms comprising corynebacteria, preferably by selectively inhibiting those corynebacteria capable of catabolising fatty acids.

It is well known that freshly secreted sweat is odourless and that body malodour is the result of a biotransformation of the sweat by microorganisms living on the surface of the skin to produce volatile odoriferous compounds.

There are three types of personal product routinely used to combat body malodour: perfumes, antiperspirants and deodorants.

Perfumes may simply mask body malodour. However perfume compositions have been disclosed which exhibit a deodorant action. EP-B-3172, EP-A-5618, U.S. Pat. No. 4,304,4679, U.S. Pat. No. 4,322,308, U.S. Pat. No. 4,278,658, US-A-4,134,838, U.S. Pat. No. 4,288,341 and U.S. Pat. No. 4,289,641 all describe perfume compositions which exhibit a deodorant action when applied to human skin fit or when included in a laundry product used to launder textiles.

Antiperspirants work by blocking the sweat glands thereby reducing perspiration.

Antimicrobial agents used in deodorants are designed to reduce the population of micro-organisms living on the surface of the skin. Typical agents of this nature include ethanol and Triclosan (2,4,4'-trichloro-2'-hydroxy-diphenyl ether) which are well known to exert in antimicrobial effects. The use of common deodorant actives results in a non-selective antimicrobial action exerted upon most of the skin's natural microflora. This is an undesirable side effect of such deodorant formulations.

Many disclosures describe compositions comprising antimicrobials which are designed to eliminate malodour by sub-lethally reducing the microflora population.

WO 95/16429 (Henkel) describes deodorant compositions comprising fat soluble partial esters of hydroxy carboxylic acids.

WO 95/07069, WO 91/11988 and WO 91/05541 (all Gillette) describe deodorant compositions comprising inhibitors of pyridoxal phosphate dependent amino acid lyase.

WO 94/14934 (Unilever) describes a method for reducing the perceptibility of an odoriferous substance using an antibody or antibody fragment. Such antibodies could be used in deodorant compositions.

WO 93/07853 (Monell) describes the use of mimics of the odoriferous compound 3-methyl-2-hexenoic acid to reduce body malodour.

DD 29 39 58 (Medezinische Fakultaet (Charite) der Humboldt Universitaet zu Berlin) describes the use of lipoxygenase Inhibitors to act biochemically to reduce sweat production or to inhibit, to various degrees, the action of skin bacteria or their enzymes on the decomposition of sweat to form unpleasant-smelling substances.

DE 43 43 265 (Henkel) describes deodorant compositions comprising saturated dioic acid (C3–C10) esters. It is claimed that the active inhibits a sweat decomposing esterase and the compositions are said not to disturb the skin's natural microflora.

DE 43 4 254 (Henkel) describes the use of lipid-soluble partial esters of hydroxy carboxylic acids in deodorant compositions.

Some disclosures describe the use of antimicrobial substances which are selective against odour producing bacteria.

WO 90/15077 (Gillette) describes the use of antibodies to a carrier or transport protein of coryneform and staphylococci. It is disclose1 that these bacteria types have an amino acid lyase enzyme which is responsible for the formation of malodour.

DE 43 39 605 (Beiersdorf) describes the use of deodorising mixtures of alpha-omega alkanedioic acids and fatty acid partial glycerides of unbranced fatty acids which may be present in a suitable cosmetic vehicle to combat Gram-positive, particularly coryneform, bacteria.

Woolwax acids have also been disclosed in the following Beiersdorf publications as deodorant actives in combination with:

alpha-omega alkanedioic acids (DE 43 24 219);

partial glycerides of unbranched fatty acids (DE 43 09 372); or monocatboxylic acids, especially unbranched fatty acids (DE 43 05 889).

Each combination is described as suitable to combat Gram-positive, especially coryneform, bacteria.

DE 4237081 (Beiersdorf) describes deodorant compositions comprising monocarboxylic acid diglycerides and/or triglycerides. The compositions are said to be suitable against Gram-positive, especially coryneform, bacteria.

EP-A-0 697 213 (Beiersdorf) describes the selective reduction of coryneform bacteria using a mixture of:

lauric acid;

one other fatty acid C6–C20 (one of which must be at least C12);

glyceryl monocaprate/glyceryl monocaprylate;

without the use of ethoxylated glyceryl fatty acid esters and propoxylated glyceryl fatty acid esters;

which has a pH of less than B.

WO 94/07837 (Unichema) describes certain novel unsaturated dioic acids having between 8 and 22 carbon atoms. Also described is their potential use to treat malodour.

EP-A-0 750 903 (Cooperatie Cosun UA) discloses deodorant compositions comprising sugar-fatty acid esters. The actives are described as being selective towards odour causing micro-organisms. These odour-causing micro-organisms are said to be the Corynebacterium varieties known as lipophilic diphtheroids such as *Corynebacterium xerosis* and *C. minutissimum*.

Coryneform is a designation of a large ill-defined group of bacteria. The diverse genera that have been included with the coryneforms include Actinomyces, Arachnia, Arcanobacterium, Arthrobacter, bacterionema, Bifidobacteriurn, Brevibacterium, Cellulomonas, Corynebacterium. Eyrsipelothrix, Eubacteriumr. Kurthia, Listeria, Mycobacterium, Nocardia, Oerskovia, Propionibacterium, Rhodococcus and Rothia.

It is clear that the majority of previous disclosures in this area have been aimed at antibacterial or bacteriostatic effects towards the whole skin flora or selected species.

Without being bound by theory we believe that the Corynebacterium genus can be subdivided into two subgroups according to ability to catabolise fatty acids. We further believe that one of these subgroups, hereinafter referred to as "Corynebacteria A" which is capable of catabolising fatty acids, contributes strongly to the formation of body malodour, in particular axillary malodour. The other subgroup, hereinafter referred to as "Corynebacteria B", which catabolises fatty acids much less so or not at all, contributes much less or even not at all to malodour formation. We also believe that it is possible to selectively inhibit the generation of odorous metabolites by Corynebacteria A.

The deodorants available on the market tend to be insufficiently effective and/or substantially reduce the numbers of all bacteria in the microflora indiscriminately. The present invention offers the opportunity to provide deodorant products which for many females will substantially reduce malodour formation while inhibiting only a minor portion of the microflora. For many males malodour formation can be substantially reduced or even largely eliminated by inactivating the Corynebacteria A.

Furthermore, we have found a range of perfume components capable of selectively inactivating Corynebacteria A, while leaving other bacteria, notably Corynebacteria B much less affected or even not notably affected at all. Significant deodorant action can be obtained by the action of these components singly or in combination.

Accordingly, the invention provides a cosmetic method for reducing or preventing body malodour by topically applying to human skin a composition comprising an active agent capable of inactivating body malodour-causing microorganisms comprising corynebacteria, wherein the agent is a perfume component which is capable of inactivating the corynebacteria capable of catabolising fatty acids.

The invention also provides the use of a perfume component to inactivate the corynebacteria capable of catabolising fatty acids.

The invention further provides the use of a perfume composition, comprising at least 30% by weight of one or more perfume components capable of inactivating the corynebacteria capable of catabolising fatty acids, to reduce body malodour.

The invention further provides the use of a deodorant product comprising a perfume component to reduce body malodour by inactivating the corynebacteria capable of catabolising fatty acids.

The invention further provides a perfume composition comprising at least 30% by weight of one or more of the following perfume components; (Z)-3,4,5,6,6-pentmethylhept-3-en-2-one, mixtures of diethyl- and dimethyl-cyclohex-2-en-1-one, citronellol, 2-methyl-3-(4-(1-methylethyl)phenylpropanal, (2-(methytoxy)4-propyl-1-benzenol), diphenyltmethane, tetrahydrolinalol, 4-(4-methyl-3-pentenyt)cyclohex-3-ene-1-crbaldehyde, 3-(4-methyl-3-pentenyl)cyclohex-3-ene-1-carbaldehyde, 3-(1,3-benzodioxol 5-5-yl2-methylprooanal, α-ionone, β-ionone, tricycdo[5.2.1.0,2,6]dec-4-en-8-yl ethanoate, 4-(4-hydroxy4-methylpentyl)cyclohex-3-enecarbaldehyde, 3-(4-hydroxy4-methylpentyl)-cyclohex-3-enecabaldehyde methyl iso-eugenol, 2-(1,1-dimethylethyl)cyclohexyl ethanoate, 4-(1,1-dimethylelhyi)cyclohexylethanoate, 4-methyl-2-(2-methylprop-1-enyl) tetrahydropyran, and a deodorant product comprising such a perfume composition.

The invention still further provides a method of producing a perfume composition which comprises (i) evaluating perfume components on the ability to inhibit fatty acid metabolism in corynebacteria, (ii) selecting perfume components on the ability to sub-lethally inhibit fatty acid metabolism in corynebacteria, and (iii) mixing together two or more of said selected perfume components, optionally with other perfume components.

The term "perfume component" is used herein to represent a material which is added to a perfume to contribute to the olfactive properties of the perfume. A perfume component can be acceptably employed to provide odour contributions to the overall hedonic performance of products. Typically, a perfume component will be generally recognised as possessing odours in its own right, will be relatively volatile and often has molecular weight within the range 100 to 300. Typical materials which are perfume components are described in "Perfume and Flavour Chemicals", Volumes I and II (Steffan Arctander, 1969). A perfume composition will contain a number of individual perfume components, and optionally a suitable diluent The concentration of perfume components referred to herein is relative to the total concentration of perfume components present in the composition, ie excludes any diluent The perfume components used in the present invention are capable of inactivating Corynebacteria, preferably selectively inactivating Corynebacteria A. By inactivate is meant any sub-lethal effect resulting in a reduction or elimination of the production of odoriferous metabolites, eg by modification of bacterial metabolism, such as fatty acid metabolism. The sub-lethal effect of a perfume component preferably occurs at concentrations below its minimum inhibitory concentration, determined as described in Example 2 below.

In particular, by sub-lethal is meant a significant inhibition of metabolism, e.g. pentadecanoic acid utilisation (at least 60% inhibition), preferably without concomitant reductions in cell viability (not more than 1 $\log_{10}$ CFU/ml reduction) and glucose utilisation (not more than 10% reduction).

The perfume components used in the present invention may be incorporated into deodorant products which include, but are not limited to, body deodorants and antiperspirants including roll ons, gel products, stick deodorants, antiperspirants, shampoos, soap shower gets, talcum powder, hand cream, skin conditioners, sunscreen, sun tan; lotion, skin and hair conditioners.

The perfume components may also be usefully employed for deodorant properties by incorporation into other products, for example, in laundry and household products such as rinse conditioners, household cleaners and detergent cleaners. The perfume components can be incorporated into textiles themselves during their production using techniques known in the art, to provide deodorant protection.

It is postulated that the preferred selective inhibition of Corynebacteria A is achieved by inhibiting the metabolic pathways of the Corynebacteria A which leads to a reduction in the production of malodorous metabolites. The inhibition of the metabolic pathway of Corynebacteria A is more important than the inhibition of the metabolic pathway of Corynebacteria B, as only the Corynebacteria A are capable of producing malodorous products.

In a preferred method according to the invention, perfume components which selectively inhibit the metabolic pathway of only those corynebacteria capable of catabolising fatty acids are used, by which is meant inactivating Corynebacteria A to a significantly higher degree than Corynebacteria B. Preferably, it means inactivating Corynebacteria A to a significantly higher degree than the majority, preferably at least 75%, more preferably at least 90% of bacteria, other than Corynebacteria A constituting the skin microflora.:

The levels of perfume materials used in a skin product may lead to general bacteriostatic and bactericidal effects. A skilled person responsible for formulating a finished product will be able to adjust the level to produce the desired effect in the final product.

The perfume components employed in the present invention are more active with Corynebacteria A than with other bacteria constituting the axillary microflora, including Corynebacteria B, when considering the selective inhibition of the metabolic pathway of the bacteria, particularly in respect of fatty acid metabolism.

The active perfume components preferably selectively inhibit the metabolic pathway of Corynebacteria A, leading to a reduction of malodorous compounds, producing a deodorant effect in consumer products. In a preferred method according to the invention, an Odour Reduction Value, measured as described in Example 4, of at least 10%, more preferably at least 30%, and particularly at least 50% is obtained. The active components may be mixed with other perfume components to deliver perfumes or perfume compositions with the desired deodorant and hedonistic properties. To deliver high deodorant effects the active components preferably comprise 30% or more of the total perfume formulation by weight, more preferably at least 40% and particularly at least 60%. A deodorant product preferably comprises at least 0.05% to 4%, more preferably 0.1% to 2% by weight of the active perfume components. Preferred actives include the following perfume components.

(Z)-3,4,5,6,6-pentamethylhept-3-en-2-one (Acetyl di iso amylene)

Mixture of diethyl- and dimethylcyclohex-2-en-1-one (Azarbre)

Citronellol 2-methyl-3-(4-(1-methylethyl)phenyl)propanal (Cyclamen aldehyde)

(2-(methyloxy)4-propyl-1-benzenol) (Dihydroeugenol)

Diphenylmethane

Tetrahydrolinalol 4-(4-methyl-3-pentenyl)cyclohex-3-ene-1-carbaldehyde (Empetaal)

3-(4-methyl-3-pentenyl)cyclohex-3-ene-1-carbaldehyde (Empetaal)

3-(1,3-benzodioxol-5-yl)-2-methylpropanal (Helional)

α- and β-Ionone and mixtures thereof (Ionone)

5 tricyclo[5.2.1.0 2,6]dec4-en-8-yl ethanoate (Jasmacylene), 4-(4-hydroxy-4-methylpentyl)cyclohex-3-enecarbaldehyde (Lyral)

3-(4-hydroxy-4-melhyloentyl)cyclohex-3-enecarbaldehyde (Lyral)

Methyl iso-eugenol 2-(1,1-dimethylethyl)cyclohexyl ethanoate (Ortholate)

4-(1,1-dimethylethyl)cyclohexyl ethancztc (Ortholate)

4 Methyl-2-(2-methylprop-1-enyl)tetrahydropyran (Rose oxide)

A perfume composition for use in the present invention preferably comprises at least 5, more preferably at least 10, and particularly at least 15 of the above perfume components.

The invention is illustrated by the following examples.

EXAMPLE 1

A demonstration of fatty acid catabolism in an isolated pure culture of Corynebacterium A deposited as NCIMB 13590 (deposited under the Budapest Treaty with National Collections of Industrial and Marine Bacteria Ltd, 23 St Machar Drive, Aberdeen Scotland, UK on Jun. 28, 1999) was determined in vitro using the method given below:

The in vitro model system, reproducing fatty acid catabolism by axillary bacteria, consisted of 250 ml baffled shake flasks, to which were added 30 ml semi-synthetic medium (see below) supplemented with fatty acid substrate (2.0 mg/ml pentadecanoic acid) This system was employed to evaluate selected potential deodorant actives (see below). Flasks were inoculated with fresh bacterial biomass, pregrown for 24 h in TSBT (see below), to give starting optical densities ($A_{500}$) of 1.0–2.0. Following inoculation, flasks were incubated aerobically at 35° C., with agitation (130 rpm), and analysed after 24 h. Culture viability/purity was determined by TVC analysis on TSAT plates (see below) following serial dilution in quarter-strength Ringers solution.

Fatty acid levels In the flasks were determined by capillary gas chromatography (GC) analysis. Initially, 5.0 ml aliquots from each flask were rapidly transferred into universal tubes: an internal standard (1.0 mg/ml lauric acid) was added to each universal tube and the culture medium was acidified (pH-2) by the addition of hydrochloric acid. Liquid-liquid extraction was then carried out using 2 vol (10 ml) ethyl acetate; organic and aqueous phases were resolved by centrifugation (2000 rpm, 3 min). 2.0 ml of each organic (upper) phase was then transferred to a sampling tube prior to analysis on a Perkin Elmer 8000 (Series 2) GC fitted with a 15 m×0.32 mm (internal diameter) FFA (nitroterephthalic acid modified PEG/siloxane copolymer) fused silica capillary column (film thickness 0.25 mm) (Quadrex). This column was attached to the split splitless injector and flame ionisation detector (FID) of the GC; injector and detector temperatures were each 300° C. Carrier gas for the column was helium (6.0 psi), while hydrogen (17 psi) and air (23 psi) were supplied the FID. The temperature programme for fatty acid analysis was 80° C. (2 min); 80–250° C. (20° C./min); 250° C. (5 min). Sample size injection was 0.5–1.0 μl. Fatty acid levels in the flasks were quantified by comparison of peak areas with known levels of both internal (lauric acid) and external (pentadecanoic acid) standards.

EXAMPLE 2

The minimum inhibitory concentration of perfume components was determined by the following method.

A fresh culture of of the test inoculum (Corynebacteria xerosis NCTC 7243 (National Collection of Type Cultures. Public Health Laboratory Service, Central Public Health Laboratory .61 Colindale Avenue. London)) diluted in sterile 0.1% special peptone solution to give a concentration of approximately $10^6$ cfu/ml was prepared Test samples were diluted in sterile trptone soya broth (TSB) Each row of the microtitre plate (labelled A-H) was allocated to one sample, i.e. eight samples per plate. Row 8 (H) contained only TSB for use as a bacterial control to indicate level of turbidity in the absence of test material. Aseptically 200 μl of the initial dilution was transferred to the 1st and 7th well of the appropriate row. All other test wells were filled with 100 μl of sterile TSB using an 8 channel pipette. The contents of all wells in column 1 were mixed by sucking samples up and down pipette tips before 100 μl was transferred to column 2. The same sterile pipette tips can be used to transfer 100 μl of each well in column 7 in to the appropriate well in column 8. Tips were discarded into disinfectant solution. Using fresh sterile tips the process was repeated by transferring 100 μl from column 2 into column 3 (and 8 into 9). The process was continued until all wells in columns 6 and 12 contained 200 µl. After mixing 100 µl was discarded from wells in these columns to waste.

To all wells 100 µl of pre-diluted test culture was added giving 200 µl final volume in each well.

A blank plate was prepared for each set of samples using the above protocol-except 100 µl of sterile 0.1% peptone was added instead of bacterial culture.

Plates were sealed using autoclave tape and incubated overnight at 35° C.

The reader was preset to gently agitate the plates to mix the contents before reading absorbance at 540 nm. The control plate for each set of samples was read first. The reader was then reprogrammed to use the control readings to blank all other plate readings of the set of test materials (i.e. removing turbidity due to perfume and possible colour changes during incubation) thus only printing out absorbances due to turbidity resulting from bacterial growth. Limits were set so that degrees of turbidity were given a rating.

The MIC was taken as the level of sample required to inhibit growth completely (change in absorbance <0.2).

EXAMPLE 3

Demonstration of sub-lethal inactivation of fatty acid catabolism was performed with the following in vitro method.

Prior to inoculation, flasks were supplemented with selected perfume components, at a range of concentrations (eg 500 ppm and 1000 ppm) below their predetermined minimum inhibitory concentration, to determine their ability to sublethally inhibit fatty acid catabolism by Corynebacteria A (NCIMB 13590). Stock active solutions/emulsions were prepared in semi-synthetic medium (see below), emulsions were formed by ultra-homogenisation at 24,000 rpm for ~1 min. At the end of each experiment, viability and fatty acid levels in the experimental flasks were compared to those in a control flask. Sub-lethal inhibition of fatty acid catabolism was defined as significant inhibition of pentadecanoic acid utilisation, without concomitant reductions in cell viability.

Composition of Tween-supplemented Tryptone soya brothlagar (TSBT, TSAT) used for growth/maintenance of axilary bacteria (g/l):Tryptone soya broth (30.0), Yeast extract (10.0), Tween 80 (1.0), ±Agar (20.0). Composition of semi-synthetic medium used in 10 laboratory systems simulating fatty acid catabolism by axillary bacteria (g/l): $KH_2PO_4$ (1.6), $(NH_4)_2HPO_4$ (5.0), $Na_2SO_4$ (0.38), Yeast Nitrogen Base (Difco) (3.35). Yeast Extract (0.5), Tween 80 (0.2). Triton X-100 (0.2), $MgCl_2$, $6H_2O$ (0.5), Pentadecanoic acid (2.0).

The results below show the perfume components that are active and inactive with regard to the inhibition of fatty acid metabolism in Corynebacteria A.

| Inhibition of long chain fatty acid metabolism observed | No inhibition of long chain fatty acid metabolism observed |
|---|---|
| (Z)-3,4,5,6,6-pentamethylhept-3-en-2-one | Aldehyde C11 |
| Mixture of diethyl- and dimethyl-cyclohex-2-ene-1-one | Anisic Aldehyde |
| 2-methyl-3-4-(1-methylethyl)phenyl)propanal | Caryophyllene |
| (2-(methyloxy)-4-propyl-1-benzenol) | Cinnamic alcohol |
| Diphenylmethane | 2H-2-chromenone |
| 4-(4-methyl-3-pentenyl)cyclohex-3-ene-1-carbaldehyde | |
| 3-(4-methyl-3-pentenyl)cyclohex-3-ene-1-carbaldehyde | Florocyclene |
| | 3a,4,5,6,7,7a-hexahydro-4,7-methano-1H-inden-6-yl-propanoate |
| 3-(1,3-benzodioxol-5-yl)-2-methylpropanal | 4,6,6,7,8,8-hexamethyl-1,3,4,6,7,8-hexahyd rocyclopenta[gamma]isochromene |
| Mixture of alpha and beta ionone | Hexyl cinnamic aldehyde |
| 4-(4-hydroxy-4-methylpentyl)cyclohex-3-ene carbaldehyde | |
| 3-(4-hydroxy-4-methylpentyl)cyclohex-3-ene carbaldehyde | hexyl 2-hydroxy-1-benzene carboxylate |
| Methyl-iso-eugenol | Iso-e-super |
| 2-(1,1-dimethylethyl)cyclohexyl ethanoate | Lilial |
| 4-Methyl-2-(2-methylprop-1-enyl)-tetrahydropyran | Thyme red |

EXAMPLE 4

The following are typical formulations of deodorant produces which comprise a perfume or perfume component capable of inhibiting the production of body malodour by micro-organisms comprising Corynebacteria. These formulations are made by methods common in the art.

Deodorant Sticks

Content (% by weight)

| Ingredient | Formulation 1A | Formulation 1B |
|---|---|---|
| Ethanol | | 8 |
| Sodium Stearate | 7 | 6 |
| Propylene glycol | 70 | 12 |
| Perfume | 1.5 | 2 |
| PPG-3 Myristyl ether | | 28 |
| PPG-10 Cetyl ether | | 10 |
| Cyclomethicone | | 34 |
| Silica | | |
| Water | 21.5 | |

Aerosols content % by weight

| Ingredient | Formulation 2A | Formulation 2B |
|---|---|---|
| Ethanol B | up to 100 | |
| Propylene glycol | as required | |
| Perfume | 2.5 | 1.5 |
| Chlorhydrol microdry | | 31.8 |
| Silicone Fluid DC344 | | up to 100 |
| Bentone gel IPP | | 13.65 |
| Irgasan DP300 | 0.03 | |
| Dimethyl ether | 20 | |
| Concentrate | | 22 |
| Water | 23 | |

Roll ons

Content % by weight

| Ingredient | Formulation 3A | Formulation 3B |
|---|---|---|
| Ethanol | to 100% | 60 |
| Klucel MF | | 0.65 |
| Cremphor RM410 | | 0.5 |

-continued

Roll ons

| Ingredient | Content % by weight | |
|---|---|---|
| | Formulation 3A | Formulation 3B |
| Perfume | 0.5 | 1 |
| AZTC* | 20 | |
| Cyclomethicone | 68 | |
| Dimethicone | 5 | |
| Silica | 2.5 | |
| Water | | 37.85 |

*Aluminium zirconium tetrachlorohydro glycinate

Two perfume compositions embodying this invention were made and tested for deodorant action in an underarm product, using an Odour Reduction Value test generally as described in U.S. Pat. No. 4,278,658, but with the substitution of the perfumed soap by perfumed roll-on product, using the formulation described in Formulation 3B. These perfume compositions and the method for an Odour Reduction Value test are set out below.

| | Composition by % | |
|---|---|---|
| | Perfume A | Perfume B |
| Acetyl di iso amylene | 10 | 7 |
| Adoxal | | 0.5 |
| Amberlyn super PM 577 10% DPG | 3 | |
| Azarbre | 3.5 | |
| Benzyl acetate extra | 8 | 8 |
| Benzyl salicylate | 8 | 12 |
| Cassis base | | 5 |
| Citral lemarome | | 3 |
| Citronellol pure | | 15 |
| Cyclamen aldehyde | | 5 |
| Dihydro jasmone | 0.5 | |
| Diphenyl methane | 3 | |
| Dupical | | 0.3 |
| Helional | | 4 |
| Ionone | 15 | |
| Jasmacyclene | 3 | |
| Ligustral 10% DPG AAA 1486 | 3 | |
| Lyral | 8 | 15 |
| Methyl iso eucenol | 5 | |
| Methyl octyl acetaldehyde 10% DPG AA 1918 | | 2 |
| Ortholate | | 8 |
| Para tert butyl cyclo hexyl acetate | 12 | |
| Phenyl ethyl alcohol | 12 | 13 |
| Roseacetone | 6 | 2.2 |

The Odour Reduction Value test was carried out using a panel of 40 Caucasian male subjects. A standard quantity (approximately 0.4g) of a roll-on product containing one of the perfume compositions or an unperfumed control was applied to the axillae of the panel members in accordance with a statistical design.

After a period of five hours the axillary odour was judged by three trained female assessors who scored the odour intensity on the 0 to 5 scale, as shown below.

| Score | Odour level | Conc. of aqueous isovaleric acid (ml/l) |
|---|---|---|
| 0 | No odour | 0 |
| 1 | Slight | 0.013 |

-continued

| Score | Odour level | Conc. of aqueous isovaleric acid (ml/l) |
|---|---|---|
| 2 | Definite | 0.053 |
| 3 | Moderate | 0.22 |
| 4 | Strong | 0.87 |
| 5 | Very Strong | 3.57 |

Average scores for each test product and the control product were then determined and the score for each test product was subtracted from the score for the control product to give the Odour Reduction Value.

| Average panel score perfume A | 2.08 |
|---|---|
| Control panel score | 2.31 |
| Odour Reduction Value perfume A | 0.23 |
| Odour Reduction Value as percentage of control score | 10% |

Difference for significance @95% 0.21
Difference for significance @99% 0.28

| Average panel score perfume B | 1.98 |
|---|---|
| Control panel score | 2.31 |
| Odour Reduction Value perfume B | 0.33 |
| Odour Reduction Value as percentage of control score | 14% |

Difference for significance @99% 0.21
Difference for significance @99% 0.28

Perfume A contained 47.5% and perfume B contained 54% of active perfume components.

What is claimed is:

1. A method of producing a perfume composition which comprises (i) evaluating perfume components on the ability to inhibit fatty acid metabolism in corynebacteria, (ii) selecting perfume components on the ability to sub-lethally inhibit fatty acid metabolism in corynebacteria, and (iii) mixing together two or more of said selected perfume components, optionally with other perfume components, the selected perfume components being chosen from the group consisting of (Z)-3,4,5,6,6-pentamethylhept-3-en-2-one, mixtures of diethyl- and dimethyl-cyclohex-2-en-1-one, citronellol, 2-methyl-3-(4-(1-methylethyl)phenyl)propanal, (2-(methyloxy)-4-propyl-1-benzenol), diphenylmethane, tetrahydrolinalol, 4-(4-methyl-3-pentenyl)cyclohex-3-ene-1-carbaldehyde, 3-(4-methyl-3-pentenyl)cyclohex-3-ene-1 carbaldehyde, 3-(1,3-benzodioxol-5-yl)-2-methylpropanal, α-ionone, β-ionone, tricyclo[5.2.1.0,2,6]dec-4-en-8-yl ethanoate, 4-(4-hydroxy-4-methylpentyl)cyclohex-3-enecarbaldehyde, 3-(4-hydroxy-4-methylpentyl)-cyclohex-3-enecarbaldehyde, methyl iso-eugenol, 2-(1,1-dimethylethyl)cyclohexyl ethanoate, 4-(1,1-dimethylethyl) cyclohexyl ethanoate, 4-methyl-2-(2-methylprop-1-enyl) tetrahydropyran.

2. The method of selectively inactivating corynebacteria capable of catabolizing fatty acids and causing body malodour which comprises contacting said corynebacteria withan effective amount of a perfume component which selectively inactivates said corynebacteria whereby body malodour is prevented or reduced, said corynebacteria being contacted with a perfume composition which includes at least 30% by weight of one or more perfume components capable of selectively inactivating said corynebacteria.

3. The method of selectively inactivating corynebacteria capable of catabolizing fatty acids and causing body malodour which comprises contacting said corynebacteria with an effective amount of a perfume component which selectively inactivates said corynebacteria whereby body malodour is prevented or reduced, the perfume component being selected from the group consisting of (Z)-3,4,5,6,6-pentamethylhept-3-en-2-one, mixtures of diethyl- and dimethyl-cyclohex-2-en-1-one, citronellol, 2-methyl-3-(4-(1-methylethyl)phenyl)propanal, (2-(methyloxy)-4-propyl-1-benzenol), diphenylmethane, tetrahydrolinalol, 4-(4-methyl-3-pentenyl)cyclohex-3-ene-1-carbaldehyde, 3-(4-methyl-3-pentenyl)cyclohex-3-ene1-carbaldehyde, 3-(1,3-benzodioxol-5-yl)-2-methylpropanal, α-ionone, β-ionone, tricyclo[5.2.1.0,2,6]dec-4-en-8-yl ethanoate, 4-(4-hydroxy-4-methylpentyl)cyclohex-3-enecarbaldehyde, 3-(4hydroxy-4-methylpentyl)-cyclohex-3-enecarbaldehyde, methyl isoeugenol, 2-(1,1-dimethylethyl)cyclohexyl ethanoate, 4-(1,1-dimethylethyl)cyclohexyl ethanoate, 4-methyl-2-(2-methylprop-1-enyl)tetrahydropyran.

4. The method of claim 3, which comprises contacting said corynebacteria with a perfume composition comprising at least 5 perfume components selected from said group.

* * * * *